United States Patent [19]

Worrick, III et al.

[11] Patent Number: 4,990,148
[45] Date of Patent: Feb. 5, 1991

[54] THIN FOOTPLATE RONGEUR

[75] Inventors: Charles B. Worrick, III, Hanson; John A. Santangelo, East Freetown, both of Mass.

[73] Assignee: Codman & Shurtleff, Inc., Randolph, Mass.

[21] Appl. No.: 297,141

[22] Filed: Jan. 13, 1989

[51] Int. Cl.⁵ ............................................. A61B 17/16
[52] U.S. Cl. ........................................ 606/83; 606/79; 606/170
[58] Field of Search ................... 606/53, 79, 83, 169, 606/170

[56] References Cited

U.S. PATENT DOCUMENTS

| | | | |
|---|---|---|---|
| 1,040,523 | 10/1912 | De Vilbiss | 606/83 |
| 3,752,161 | 8/1973 | Bent | 606/79 X |
| 3,835,860 | 9/1974 | Garretson | 606/79 |
| 4,499,899 | 2/1985 | Lyons, III | 606/170 |
| 4,586,497 | 5/1986 | Papra et al. | 606/79 X |
| 4,777,948 | 10/1988 | Wright | 606/83 |

FOREIGN PATENT DOCUMENTS 1053824  11/1983  U.S.S.R. .

Primary Examiner—Robert A. Hafer
Assistant Examiner—Lynda M. Cofsky

[57] ABSTRACT

A rongeur with special features applied to the footplate area to prevent the intersection of stress fields to allow the rongeur to be reduced in size and mass without materially reducing the strength of the rongeur. A transverse groove is used at the intersection of the anvil surface of the base plate and the shank base plane. Also the base of the footplate recess is offset from the shank base plane and the inside wall of the recess meets the recess base in a gentle curve. These features can be used individually or together to prevent the intersection of stress fields in the footplate area and thus allow the size of the footplate to be reduced without materially reducing the strength of the rongeur.

8 Claims, 3 Drawing Sheets

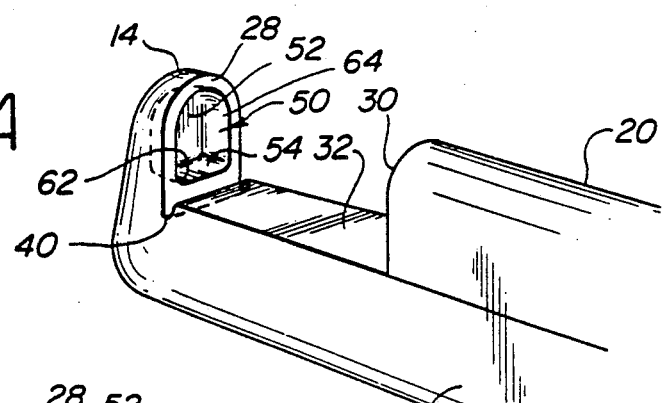
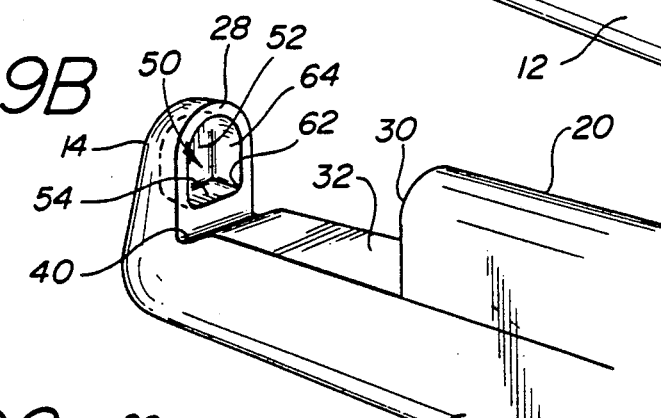
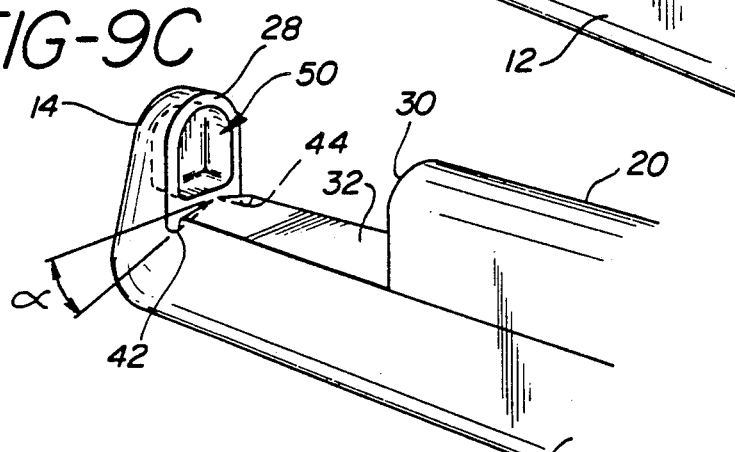
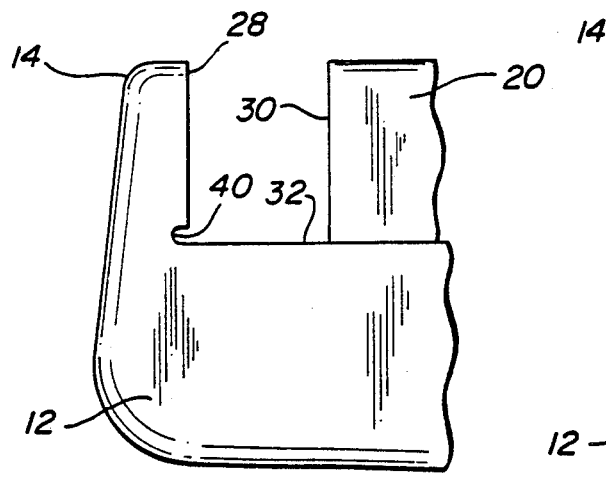
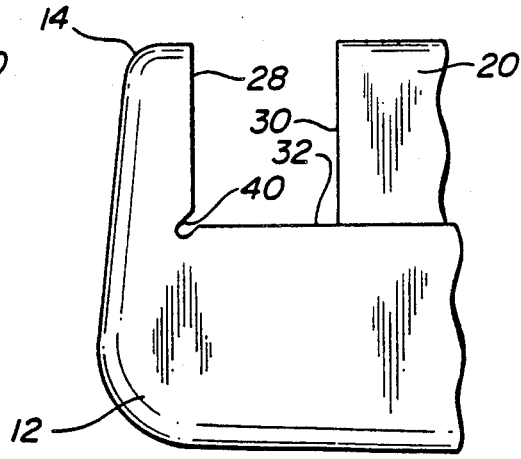

THIN FOOTPLATE RONGEUR

FIELD OF THE INVENTION

The present invention relates to a medical instrument called a rongeur and more particularly to a thin footplate rongeur.

BACKGROUND OF THE INVENTION

The rongeur is a medical instrument used for a variety of purposes. It is particularly useful for removing small amounts of bone, cartilage or other body material from inside small spaces of the knee or between vertebrae of the back. A rongeur usually includes a long fixed shank with an anvil or footplate at its distal end and a handle at its proximal end. A reciprocating shaft or crossbar moves axially with respect to the fixed shank, either inside a hollow fixed shank or along the outside surface of a rigid fixed shank. A cutter on the distal end of the reciprocating crossbar abuts the footplate to cut tissue captured between the cutter and the footplate. The proximal end of the crossbar is attached to some sort of trigger mechanism for reciprocating the crossbar and moving the cutter against the footplate.

Very large forces are experienced at the footplate of the rongeur when the surgeon is cutting hard material like bone or cartilage. Conventional rongeur designs have always had to compromise between the size and strength. It is desirable to have the footplate and the whole distal end of the rongeur as small as possible so that it can fit into the confined spaces where it is usually used. However, if one makes the footplate too small one begins to become concerned about whether the tip is strong enough withstand the forces applied to it during cutting. It would be desirable to have a rongeur with a very thin footplate portion so that it could fit into the small spaces one finds particularly in surgery of the back and still provide adequate strength for the mechanical parts of the rongeur.

SUMMARY OF THE INVENTION

The present invention provides a rongeur which is surprisingly strong for its small size. The Applicants have been able to substantially reduce the size of the rongeur in the footplate area. By carefully contouring the surfaces of the footplate to separate (i.e., to prevent) the intersection of stress fields present in the footplate and shank regions during cutting, the Applicants have been able to distribute these stresses and reduce local stress concentrations. The rongeur of the present invention, although significantly smaller then conventional rongeurs is as strong as more massive designs due to the novel features of the present invention.

A typical rongeur includes an elongated shank with a perimeter, a distal end, a proximal end, a longitudinal axis and a base plane along at least a portion of the perimeter and extending in a direction generally parallel to the longitudinal axis. The shank has a footplate at its distal end extending generally transversely to the axis of the shank from the base plane. The footplate has a proximately facing anvil surface. An elongated crossbar reciprocates axially with respect to the shank and it also has a distal and a proximal end. There is a cutting surface at the distal end of the crossbar aligned in confronting relationship to the footplate so that the footplate provides an anvil against which tissue may be cut. There is a recess in the surface of the footplate confronting the cutting means to provide a space to receive tissue during cutting. There is a handle and a trigger associated with the shank and crossbar to reciprocate the crossbar against the footplate to cut tissue. The improvement of the present invention is the inclusion of means on the base plane of the shank and the anvil surface of the footplate for preventing the intersection of stress fields in the footplate and the shank when the rongeur is placed under stress during cutting.

The recess in the footplate includes a base and a curved wall intersecting the recess base. The recess base is offset from the shank base plane a predetermined distance so that the recess and the shank base plane do not intersect. By intersection is meant a physical intersection of these surfaces in the rongeur not an intersection of the theoretical extensions of these planes into space.

In the preferred embodiment the recess base is planar and in another preferred embodiment the recess base is planar and aligned substantially parallel to the shank base plane.

Offsetting the recess base from the shank base plane helps separate the intersection of stress fields in accordance with the present invention.

Another way to help separate the intersection of stress fields is to provide a smooth curved intersection between the footplate recess wall and the footplate recess base which smooth curvature has a radius of less than one half the width of the shank in the direction transverse to the longitudinal axis of the shank.

Another feature employed in the present invention to separate the intersection of stress fields is to include a groove into the shank base plane at the intersection of the footplate anvil surface and the shank base plane at least part way across the shank base plane in the transverse direction. This groove may be a continuous groove extending all the way across the shank base of uniform depth. Alternatively, this groove may include two segments each extending from the perimeter of the shank base plane and extending at an angle to the base plane.

The footplate extends transversely from the shank and the direction of extension of the footplate may vary depending upon the intended use of the rongeur. In the preferred embodiments shown in this application the footplate extends in one embodiment at 90° to the longitudinal axis of the shank and another embodiment at an angle of 40° to the longitudinal axis of the shank.

Thus, it can be seen that the present invention provides three separate features for preventing the intersection of stress fields. The first involves separating the base of the footplate recess from the shank base plane so that the two do not intersect. The second involves providing a smooth curvature at the intersection of the recess wall and the recess base. In the preferred embodiment, this curvature is less than one half the width of the shank. The third feature involves placing a groove in the shank base plane at the intersection of the footplate anvil surface and the shank base plane. The groove extends at least part way across the shank.

These and other features and advantages of the present invention will become more apparent from the following detailed description of preferred embodiment taken in conjunction with the following drawings.

BRIEF DESCRIPTION OF THE DRAWINGS

FIGS. 9A, B and C show schematic perspective views of the tip portion of various embodiments of the present invention.

FIGS. 10A and B show partial schematic side views of other alternative embodiments of the present invention.

DETAILED DESCRIPTION OF THE PREFERRED EMBODIMENT

Figure 1:
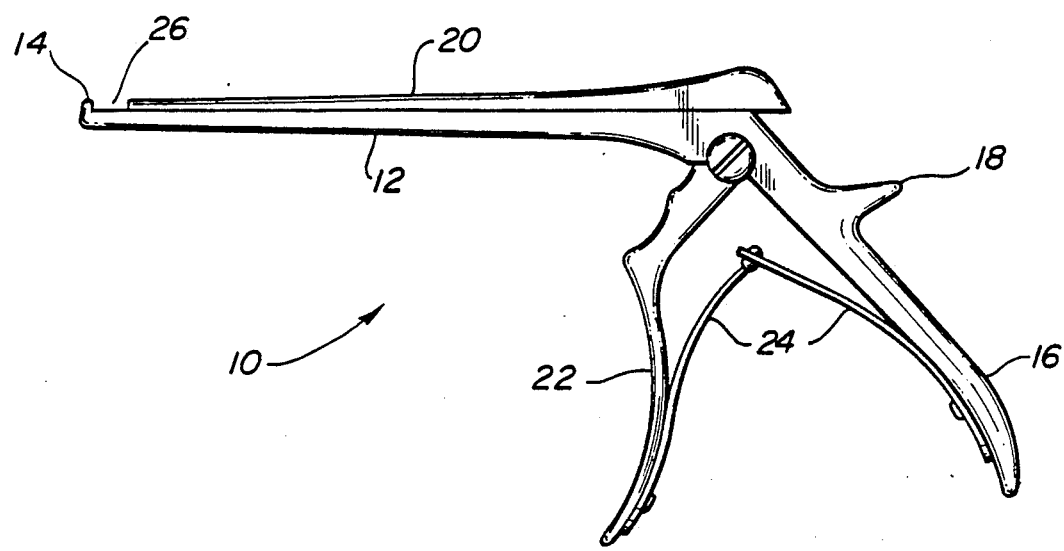
FIG. 1 shows a side elevation of a typical rongeur in which the features of the present invention may be usefully employed.

FIG. 1 shows a side view of a typical rongeur 10 which can employ the features of the present invention. Rongeur 10 has a lower shank 12 with a footplate 14 at its distal end and a handle 16 extending from its proximal end. Handle 16 includes a horn 18 which usually rests against the web between a user's thumb and forefinger. Crossbar 20 slides along lower shank 12 in response to the action of trigger 22. Spring 24 biasses trigger 22 and handle 16 apart. The distal end of crossbar 20 includes a cutting surface which mates against the confronting surface of footplate 14 to cut tissue which is placed in the jaw opening 26 between footplate 14 and crossbar 20.

The mechanical design of the rongeur parts including trigger 22, spring 24 and the mechanism for holding crossbar 20 properly aligned for reciprocation on lower shank 12 and the drive mechanism for causing this reciprocation are conventional and will not be discussed further in this application. The remainder of this application will focus on the three important features of the present invention by which the intersection of stress fields in the vicinity of footplate 14 is prevented to provide a smaller geometric shape for the footplate section without weakening the rongeur.

Figure 2:
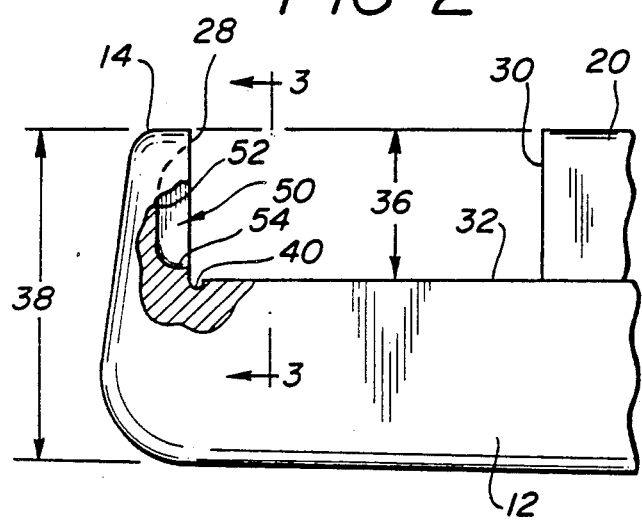
FIG. 2 shows a partial side view, partly in section, of the tip of the rongeur in FIG. 1 with a footplate extending at a 90° angle.

FIG. 2 shows a partial side view, partly in section, of the distal portion of footplate 14, lower shank 12 and crossbar 20 with footplate 14 extending transversely to lower shank 12 at a 90° angle. The proximally facing surface 28 of footplate 14 provides an anvil surface against which the distal surface 30 of crossbar 20 impacts during cutting to sever bone, cartilage or other tissue placed in jaw opening 26. Crossbar 20 slides along base plane 32 of shank 12 as can also be seen in perspective view in FIG. 9A. One use of rongeurs of this type is to cut bone or cartilage from within joint spaces of the vertebrae of the back particularly in the cervical region. It is important to have a footplate with small dimensions so that it can fit into the confined spaces between vertebrae. It is important that the axial length 34 of footplate 14 be small so that the rongeur can get behind the tissue to be cut. It is also important that the transverse height 36 of footplate 14 above base plane 32 of shank 12 be small enough to permit the footplate to enter small spaces. Transverse height 36 is also referred to as the height of the bite. It is also important that the transverse height of footplate 14 and shank 12 also be small enough to permit the insertion of the rongeur in small spaces. Transverse height 38 is also referred to as the jaw height. It should be apparent that as crossbar 20 impinges upon anvil surface 28 of footplate 14, high stresses occur at the intersection of anvil surface 28 and shank base plane 32. This stress may be reduced by preventing the intersection of these stress fields.

Referring now to FIGS. 2, 3, 9A and 9B, one feature of the present invention used to reduce stress in the footplate area is the placement of a groove 40 into shank base plane 32 at the intersection of footplate anvil surface 28 and shank base plane 32. Groove 40 may take various configurations. In a first embodiment, groove 40 is essentially U-shaped with the distal side of the U coincident with anvil surface 28 of footplate 14 with groove extending completely transversely across shank 12 at a substantially uniform depth.

In another embodiment, shown in perspective in FIG. 9B the proximal surface of groove 40 is gently blended into base plane 32.

In another embodiment, shown in perspective in FIG. 9C this groove is in two parts with a first portion 42 extending from one side of the perimeter of shank 12 toward the center line of shank 12 and disposed at an angle alpha ($\alpha$) to base plane 32. Angle alpha ($\alpha$) is not critical and in any angle between 0 and about 45° is satisfactory. A similar groove 44 extends in the opposite direction. What is important is that the distal portion of grooves 42 and 44 are coincident with anvil surface 28.

We have found that angled grooves 42 and 44 provide an easier method of placing these grooves in their proper place during manufacturing. Angled grooves 42 and 44 can be made using a file whereas it is more difficult to place a groove 40 completely across shank 12, however various well known methods are available for placing groove 40 in its proper place. The actual dimensions of groove 40 as shown in FIGS. 9A and B and grooves 42 and 44 as shown in FIG. 9C are not critical. It has been found that for rongeurs having a footplate width 46 of between 2 to 4 millimeters and having bite height 36 of between 1.9 and 3.25 millimeters and a footplate thickness 34 of between 1.5 and 2.3 millimeters with a jaw height 38 between 4.7 and 6.7 millimeters, a groove 40 having a radius of between 0.12 to 0.25 millimeters is satisfactory. These numbers are meant only to illustrate the orders of magnitude of the dimensions and are not meant to be limiting of the present invention in any way.

FIGS. 10A and B show alternative ways for placing groove 40 in shank 12. To accomplish the objective of preventing the intersection of stress fields at footplate 14 and shank 12 it would be possible to place groove 40 into the anvil surface 28 of footplate 14 as shown in FIG. 10A or at an angle into both the shank base plane surface 32 and footplate anvil surface 28. However, placing groove 40 in this orientation could impede the effectiveness of cutting. Material could be extruded into groove 40 as shown in FIGS. 10A and B when crossbar 20 impacts against anvil surface 28 leaving that extruded portion of the tissue uncut. That would be undesirable from an operational point of view for a rongeur but would still be an effective way of relieving the stress experienced at the intersection of footplate 14 and shank 12.

Figure 3:
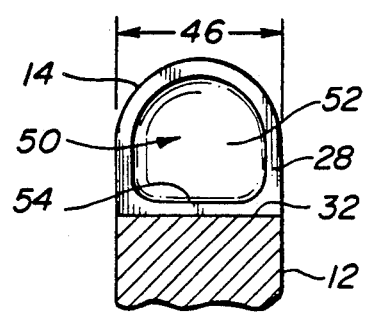
FIG. 3 shows a partial end view of the footplate portion of the rongeur of FIG. 2.
Figure 5:
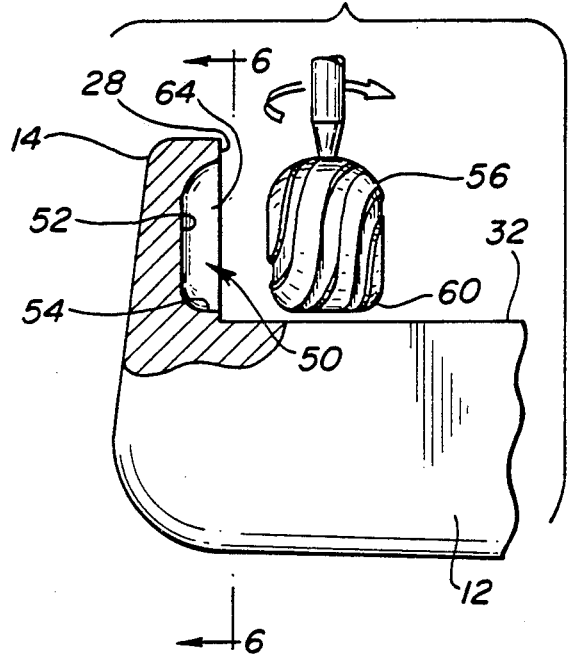
FIG. 5 shows a partial schematic view of the tip portion of the present rongeur demonstrating how a recess may be put in the footplate.
Figure 6:
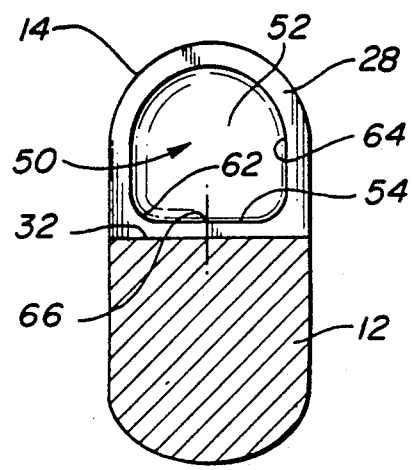
FIG. 6 shows an end view of the footplate of FIG. 5.

The remaining two stress relief features of the present invention will be discussed in connection with anvil surface 28 of footplate 14. As shown in FIGS. 2 and 3, there is a recess 50 in anvil surface 28 of footplate 14. Recess 50 has a curved surrounding wall 52 and a flat base 54 which in the preferred embodiment is aligned generally parallel to shank base plane 32. As shown in FIG. 5, recess 50 may be cut into footplate 14 using a rotating end mill 56 supported on rotating shaft 58. The perimeter of end mill 56 is curved to make the curved wall surface of 52 of recess 50. The edge 60 is rounded to provide a rounded juncture between wall surface 52 and base surface 54 throughout recess 50. It will also be noted in connection with FIGS. 3 and 6 that there is a curved intersection 62 between the inside perimeter 64 of recess 50 and base 54. Base 54 is most conveniently made flat and generally parallel to shank base plane 32, however, base 54 need be neither flat nor parallel to shank base plane 32.

It is important that curved portion 62 be used to prevent the intersection of the stress field in area 62. If this is a sharp corner, stresses will be concentrated at this point. If the radius of portion 62 is equal to one half the bite width 46 of footplate 14 then stress becomes concentrated at the center 66 of recess 50 (see FIG. 6). Thus, it is important that the radius of area 62 be less than one half bite width 46 of footplate 14.

Still referring to FIGS. 2, 3, 5 and 6, one can see that base 54 of recess 50 is raised above shank base plane 32. This is the third feature of the present invention used to prevent the intersection of stress fields in the footplate area so that the plane of base 54 and the shank base plane 32 do not intersect within the instrument. We are not talking about the imaginary projections of these planes beyond the instrument since in certain embodiments like that of FIG. 4 where footplate 14 is disposed at an angle to shank 12 these imaginary projections may intersect.

Figure 4:
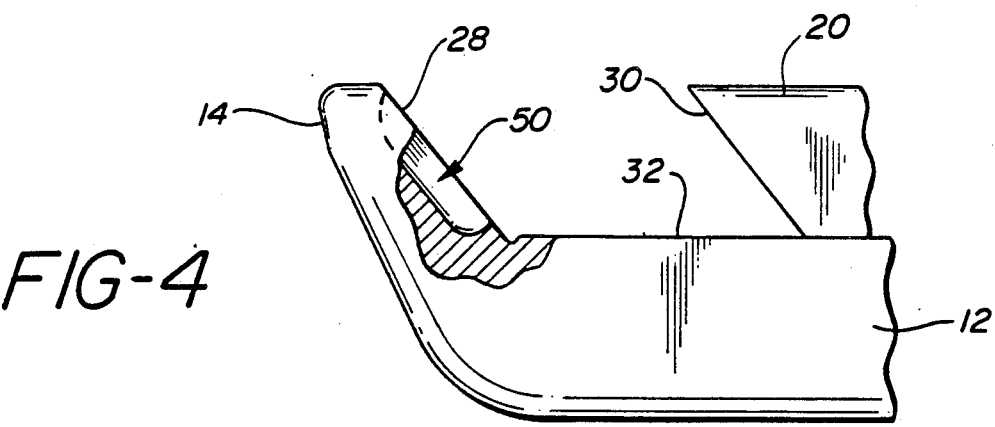
FIG. 4 shows a partial side view, partly in section, of the tip portion of an alternative embodiment of the present invention.

In FIG. 4 there is shown an alternative embodiment of a rongeur utilizing the features of the present invention where footplate 14 extends transversely from shank 12 at an angle preferably of about 40° so that the anvil surface 28 extends at an angle of about 40° to shank base plane 32. Note in FIG. 4 that the distal end 30 of crossbar 20 is angled at a similar angle to that of anvil surface 28. Forty degrees is a representative angle and any desired angle may be used. The embodiment of FIG. 4 employs a similar recess 50 in anvil surface 28 of footplate 14 similarly constructed. The base 54 of the recess shown in FIG. 4 is separated from shank base plane 32 so that they do not intersect in the instrument. A similar groove 40 as shown in FIGS. 9A or 9B or a similar pair of angled grooves 42 and 44 is shown in FIG. 9C may also be used in the embodiment of FIG. 4.

Figure 7:
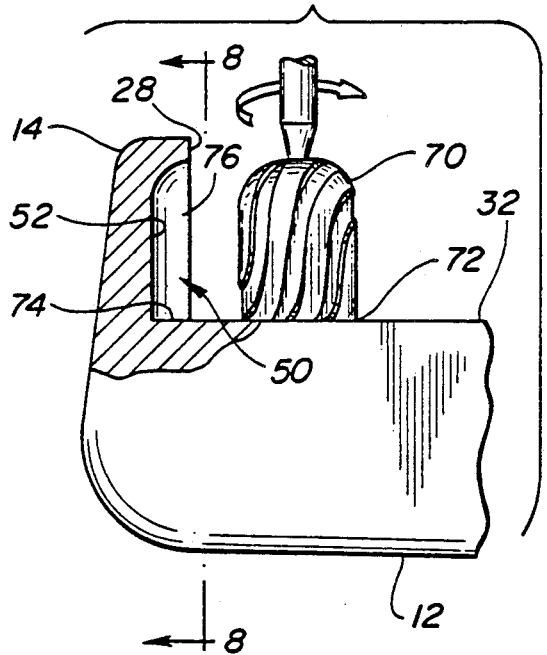
FIG. 7 shows a partial side view of the tip of a prior art rongeur showing how a recess is put in the footplate of the prior art rongeur.
Figure 8:
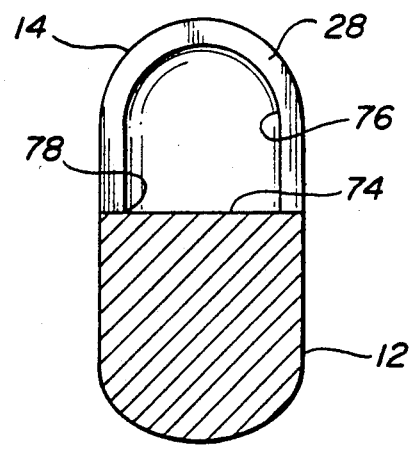
FIG. 8 shows a schematic end view of the tip portion of a rongeur shown in FIG. 7.

Referring now to FIGS. 7 and 8 there is shown a prior art embodiment of recess 50 which is cut with an end mill 70 with an edge 72 which forms a right angle to the base of end mill 70. The recesses of the prior art were also made so as to have the base 74 flush with shank base plane 32. As seen in FIG. 8 the intersection of recess base 74 and the inside perimeter 76 of anvil surface 28 meet at a sharp corner 78.

The present invention has been described in conjunction with the preferred embodiments. Those skilled in the art will appreciate that many modifications and changes may be made to the preferred embodiments without departing from the present invention. It is, therefore, not intended to limit the present invention except as set forth in the appended claims.

What is claimed:

1. In a rongeur comprising:
    an elongated shank having a perimeter, a distal end, a proximal end, a longitudinal axis and a base plane along at least a portion of said perimeter, said base plane extending in a direction generally parallel to said longitudinal axis;
    a footplate at the distal end of said shank extending generally transversely to the axis of said shank from said base plane and having a proximally facing anvil surface;
    an elongated crossbar adapted to reciprocate axially with respect to said shank and having a distal end and a proximal end;
    cutting means at the distal end of said crossbar aligned in confronting relationship to said footplate so that said footplate provides an anvil against which tissue may be cut;
    a recess in the surface of said footplate confronting said cutting means to provide a space to receive tissue during cutting;
    means operatively connecting said crossbar and said shank to permit said cutting means to reciprocate against said footplate to cut tissue;
    groove means on said base plane and on said anvil surface aligned generally transverse to said shank longitudinal axis and extending from said shank perimeter for separating the intersection of stress fields in said footplate and said shank when said rongeur is placed under stress during cutting.

2. The rongeur of claim 1 wherein said recess includes a base and a curved wall intersecting said recess base and wherein said recess base is offset from said shank base plane a predetermined distance so that said recess base and said shank base plane do not intersect.

3. The rongeur of claim 2 wherein said recess base is planar.

4. The rongeur of claim 2 wherein said recess base is planar and substantially parallel to said shank base plane.

5. The rongeur of claim 2 wherein said recess wall and said recess base join in a smooth curve having a radius of curvature less than one half the width of said shank in a direction transverse to the longitudinal axis thereof.

6. The rongeur of claim 1 wherein said means for separating the intersection of stress fields in said footplate and said shank when said rongeur is placed under stress during cutting includes:
    a groove into said shank base plane at the intersection of said footplate anvil surface and said shank base plane at least partway thereacross.

7. The rongeur of claim 6 wherein said groove includes two segments each extending from the perimeter of said shank into said shank base plane and extending at an angle to said shank base plane.

8. The rongeur of claim 1 wherein said footplate anvil surface is disposed at an angle to the longitudinal axis of said shank and the cutting means on said crossbar is aligned at a similar angle relative to the longitudinal axis of said shank so that said cutting means can cut tissue against said anvil surface.

* * * * *